United States Patent
LaRose et al.

(10) Patent No.: US 10,556,048 B2
(45) Date of Patent: Feb. 11, 2020

(54) BLOOD PUMP WITH IN-SITU ATTACHING MOTOR STATORS

(71) Applicant: HeartWare, Inc., Miami Lakes, FL (US)

(72) Inventors: Jeffrey A. LaRose, Raleigh, NC (US); Gill B. Bearnson, Salt Lake City, UT (US); Stanley P. Mack, Pinellas Park, FL (US); Charles R. Shambaugh, Coral Gables, FL (US)

(73) Assignee: HeartWare, Inc., Miami Lakes, FL (US)

( * ) Notice: Subject to any disclaimer, the term of this patent is extended or adjusted under 35 U.S.C. 154(b) by 108 days.

(21) Appl. No.: 15/791,573

(22) Filed: Oct. 24, 2017

(65) Prior Publication Data
US 2018/0110909 A1    Apr. 26, 2018

Related U.S. Application Data

(60) Provisional application No. 62/411,781, filed on Oct. 24, 2016.

(51) Int. Cl.
*A61M 1/10* (2006.01)

(52) U.S. Cl.
CPC .................................. *A61M 1/1036* (2014.02)

(58) Field of Classification Search
CPC ... A61M 1/1012; A61M 1/1036; A61M 1/125
See application file for complete search history.

(56) References Cited

U.S. PATENT DOCUMENTS

| | | | |
|---|---|---|---|
| 8,690,749 | B1 | 4/2014 | Nunez |
| 2009/0069854 | A1 | 3/2009 | Keidar et al. |
| 2009/0112312 | A1 | 4/2009 | LaRose et al. |
| 2012/0059460 | A1* | 3/2012 | Reitan ................ A61M 1/1024 623/3.12 |
| 2015/0051438 | A1 | 2/2015 | Taskin |
| 2016/0250400 | A1 | 9/2016 | Schumacher |
| 2016/0287771 | A1 | 10/2016 | Khanal et al. |

FOREIGN PATENT DOCUMENTS

CA    2947104 C    5/2017

OTHER PUBLICATIONS

International Search Report and Written Opinion dated Jun. 26, 2018 for corresponding International Application No. PCT/US2017/057969; International Filing Date: Oct. 24, 2017 consisting of 11-pages.

* cited by examiner

*Primary Examiner* — George Manuel
(74) *Attorney, Agent, or Firm* — Christopher & Weisberg, P.A.

(57) ABSTRACT

A housing having an interior and an exterior. A pump rotor is configured to be received within the interior of the housing, the pump rotor includes a magnet. A stator having a delivery configuration and an operative configuration is included, the stator in the delivery configuration has a delivery diameter, the stator in the operative configuration being configured to be disposed around the exterior of the housing and to form an assembled pump having a diameter greater than the delivery diameter.

19 Claims, 6 Drawing Sheets

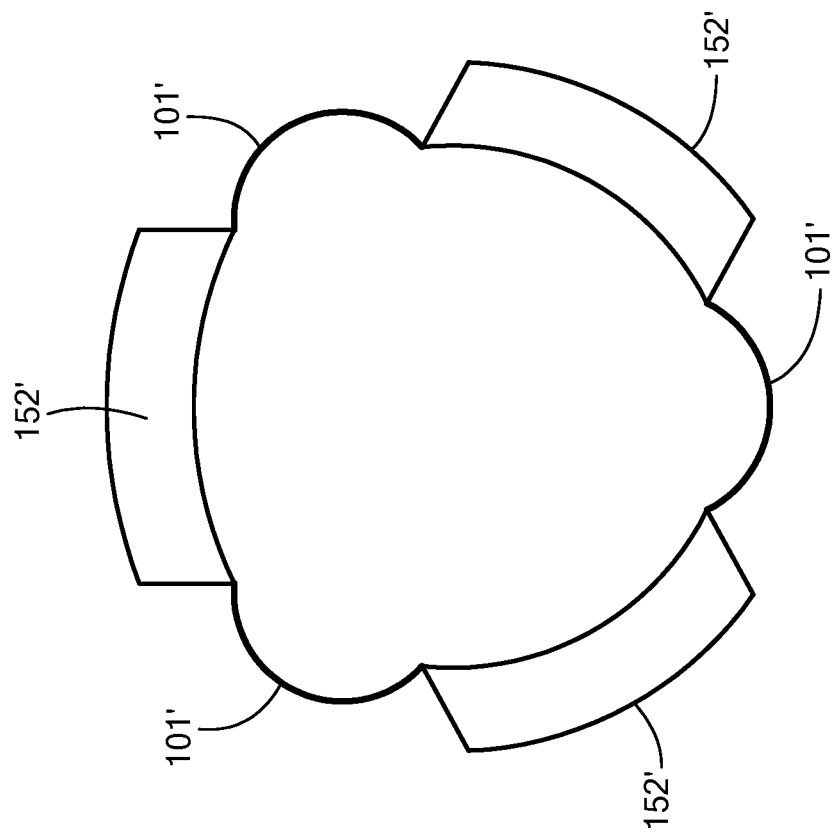
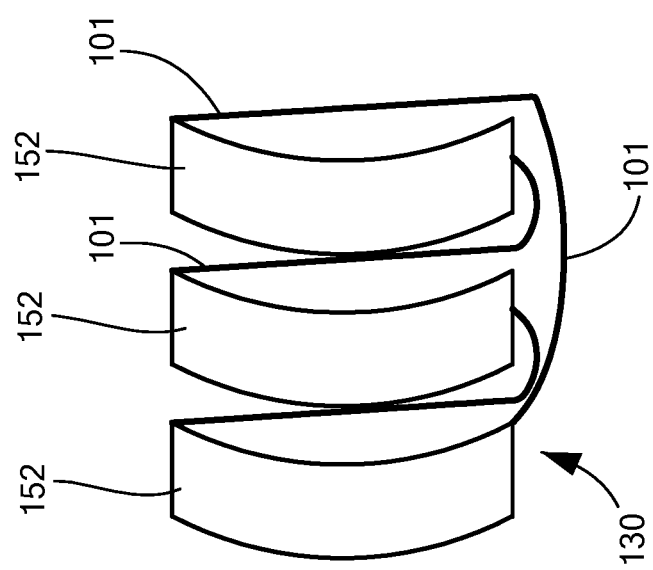

BLOOD PUMP WITH IN-SITU ATTACHING MOTOR STATORS

CROSS-REFERENCE TO RELATED APPLICATION

This application is related to and claims priority to U.S. Provisional Patent Application Ser. No. 62/411,781, filed Oct. 24, 2016, entitled BLOOD PUMP WITH IN-SITU ATTACHING MOTOR STATORS, the entirety of which is incorporated herein by reference.

STATEMENT REGARDING FEDERALLY SPONSORED RESEARCH OR DEVELOPMENT n/a

TECHNICAL FIELD

The present invention relates to mechanical circulatory support devices and methods of implanting and operating the same.

BACKGROUND

Mechanical circulatory support devices are used to assist the pumping action of the heart. A mechanical circulatory support device typically includes a pump having pump housing and a moveable element, most typically a rotor, disposed within the pump housing to impel blood through the housing. The pump is implanted within a patient with an inlet of the housing in communication with one portion of the patient's cardiovascular system and an outlet of the housing in communication with another portion of the cardiovascular system. For example, to assist the pumping action of the left ventricle, the inlet of the pump may be in communication with the interior of the left ventricle, whereas the outlet of the pump may be in communication with the aorta. One form of blood pump includes a tubular pump housing having a rotor coaxial with the housing. The rotor desirably incorporates a permanent magnet. A stator including a plurality of electrical coils is arranged around the exterior of the pump housing. In operation, electrical power is applied to the coils in sequence so as to create a rotating magnetic field within the housing. The rotating field interacts with the magnet incorporated in the rotor so as to spin the rotor about its axis and thus force blood through the pump housing. As disclosed in U.S. Published Patent Application No. 2009/0112312 ("the '312 Publication"), the disclosure of which is hereby incorporated by reference herein, it is been proposed to implant the pump within the aorta of a living subject. Pumps of this general type typically are made as permanent assemblies, with the elements of the stator fixed in position on the outside of the pump housing during manufacture and with the entire assembly enclosed within a sealed outer housing.

SUMMARY

The present invention advantageously provides a method and system for attaching motor stators in situ in blood pumps. The blood pump includes a housing having an interior and an exterior. A pump rotor is configured to be received within the interior of the housing, the pump rotor includes a magnet. A stator having a delivery configuration and an operative configuration is included, the stator in the delivery configuration has a delivery diameter, the stator in the operative configuration being configured to be disposed around the exterior of the housing and to form an assembled pump having a diameter greater than the delivery diameter.

In another aspect of this embodiment, the housing defines a housing axis and axial directions along the housing axis, the stator including a plurality of units, each unit including a coil having a coil axis and an electrical conductor arranged in one or more turns surrounding the coil axis, the stator in the operative configuration having the units disposed around the housing axis with the coil axes of the units transverse to the housing axis.

In another aspect of this embodiment, in the delivery configuration: the stator has a delivery axis, the coil axes are transverse to the delivery axis, and at least one of the units is offset from another one of the units in a direction along the delivery axis.

In another aspect of this embodiment, in the delivery configuration, the units of the stator are disposed in a row along the delivery axis, with each of the units being offset from an adjacent one of the units in a direction along the delivery axis.

In another aspect of this embodiment, the housing has an exterior surface including one or more arcuate surfaces coaxial with the housing axis, and wherein each of the units has an interior surface in the form of a partial surface of revolution around a unit axis transverse to the coil axis of that unit, the interior surfaces of each units confronting the arcuate surfaces of the housing when the stator is in the operative configuration.

In another aspect of this embodiment, the stator includes a flexible member including one or more coils, the flexible member extending around the housing when the stator is in the operative condition.

In another aspect of this embodiment, when the stator is in the operative configuration, the flexible member forms a tube and the pump housing is disposed within the tube, and wherein the flexible member is folded when the stator is in the delivery configuration.

In another embodiment, a blood pump implantation assembly includes a delivery device. A pump is mounted to the delivery device proximate a distal end thereof, the pump including a pump housing, a rotor configured to be disposed within the pump housing, and a stator. The pump in a delivery condition has the stator offset from the pump housing and has the stator define a first diameter. The delivery device is configured to transition the pump from the delivery condition to an operative condition in which the stator is in an operative configuration disposed around the pump housing and defines a second diameter larger than the first diameter.

In another aspect of this embodiment, the housing has a housing axis extending proximally and distally when the pump is in the delivery condition, the stator including a plurality of units, each unit including a coil having a coil axis and an electrical conductor arranged in one or more turns surrounding the coil axis, the pump in the operative configuration having the units disposed around the housing axis with the coil axes of the units transverse to the housing axis.

In another aspect of this embodiment, in the delivery configuration the coil axes are transverse to a major longitudinal axis of the delivery device and at least one of the units is offset from another one of the units along the major longitudinal axis.

In another aspect of this embodiment, in the delivery configuration the units of the stator are arranged successively along the major longitudinal axis.

In another aspect of this embodiment, the delivery device is configured to advance the units along the major longitudinal axis toward the pump housing to bring the pump from the delivery condition to the operative condition.

In another aspect of this embodiment, the stator includes a flexible member including one or more coils, the flexible member extending around the housing when the pump is in the operative condition.

In another aspect of this embodiment, the flexible member is a tube having a wall, the wall defining a bore and the housing being disposed within the bore when the pump is in the operative condition, the flexible member being folded along one or more fold axes when the pump is in the delivery configuration.

In another aspect of this embodiment, the pump is releasably mounted to the delivery device.

In yet another embodiment, a method of implanting a blood pump in the body of a living subject includes advancing the pump into the body of the subject to a target location, the pump being in a delivery condition in which a stator of the pump is separate from a pump housing and the pump has a delivery diameter. The pump is transitioned to an operative condition, the stator being disposed around the pump housing and the pump has an operative diameter greater than the delivery diameter when in the operative condition.

In another aspect of this embodiment, the method further includes applying electrical power to the stator to provide a rotating magnetic field within the housing while the pump is in the operative condition a rotor within the housing is rotated and the rotor impels blood through the housing.

In another aspect of this embodiment, advancing the pump into the body of the subject to a target location step includes advancing the pump through vasculature of the subject.

In another aspect of this embodiment, transitioning the pump to an operative condition includes at least one from the group consisting of retracting and advancing a portion of a delivery device, the delivery device including the stator in the delivery condition.

In another aspect of this embodiment, the delivery device defines a major longitudinal axis, and wherein the stator includes a plurality of stator units disposed successively around the major longitudinal axis.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 5 is a diagrammatic elevational view depicting elements of a pump according to a further embodiment of the invention in one condition;

FIG. 6 is a view similar to FIG. 5 depicting elements of FIG. 5 in another condition;

DETAILED DESCRIPTION

Figure 1:
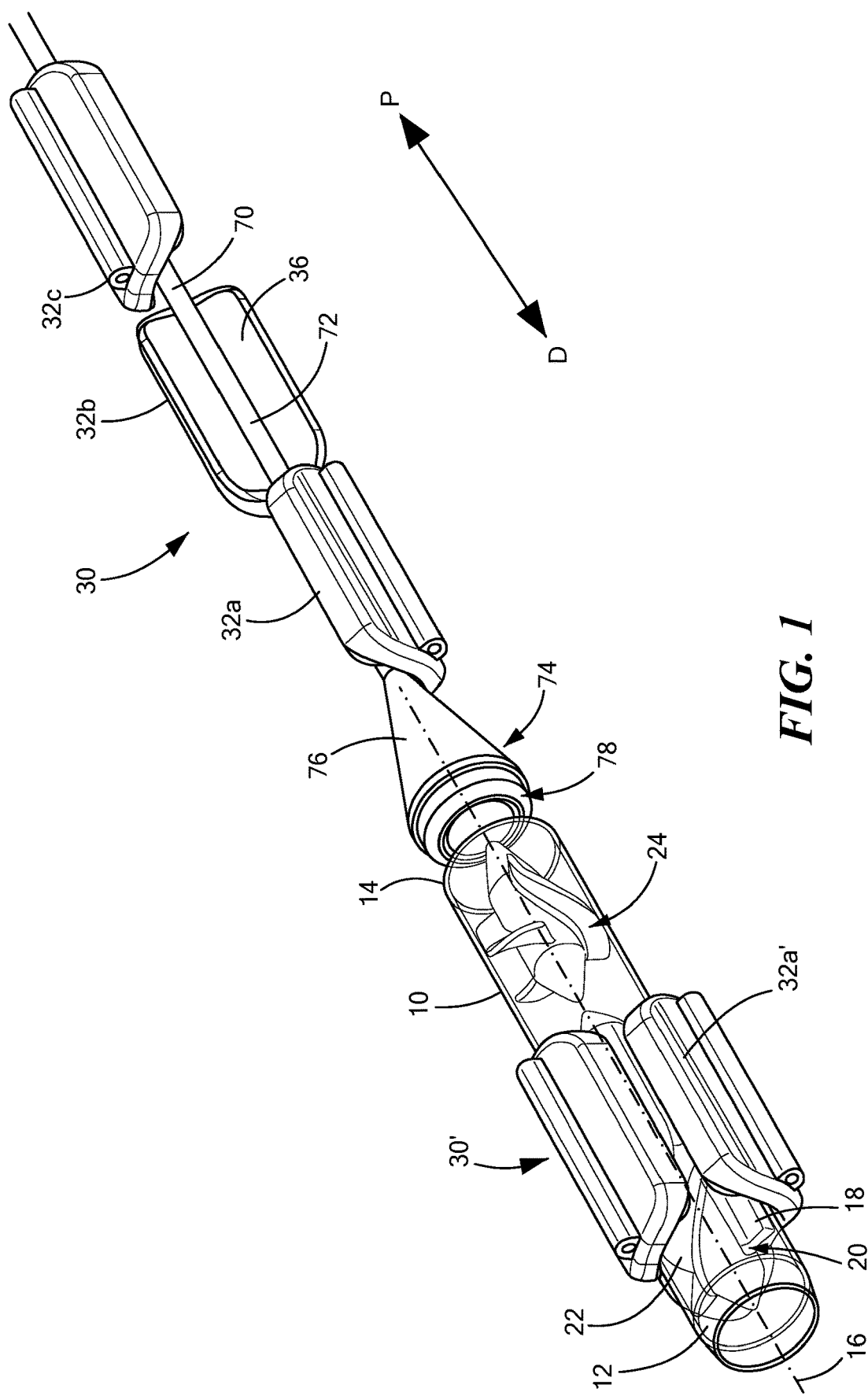
FIG. 1 is a diagrammatic perspective view depicting elements of a pump and delivery device in accordance with one embodiment of the invention.

A pump according one embodiment of the invention includes a tubular pump housing 10 (FIG. 1) having an inlet end 12 with an inlet opening and an outlet end 14 with an outlet opening. The pump housing has an interior surface defining a housing axis 16 extending between the inlet and outlet ends. The pump housing 10 also has an exterior surface generally in the form of a surface of revolution around axis 16. For clarity of illustration, pump housing 10 is depicted as transparent in FIG. 1. In practice, the pump housing 10 typically is formed from a ceramic material or other non-magnetic, biocompatible material. A rotor 18 is disposed within the interior of the pump housing. In one configuration, the rotor 18 has an axis coincident with the housing axis 16. The rotor 18 has a plurality of generally helical blades 20 defining channels 22, one of which is visible in FIG. 1. The channels 22 extend in circumferential directions around the axis of the rotor 18 and extend axially from an upstream end of the rotor 18 adjacent the inlet end 12 of the housing to the downstream end of the rotor 18. The rotor 18 incorporates a permanent magnet. For example, the rotor 18 may be formed from a single piece of a biocompatible magnetic alloy as, for example, a platinum cobalt alloy. The outer or tip surfaces of the rotor 18 adjacent the wall of the pump housing desirably define hydrodynamic bearing surfaces capable of suspending the rotor out of contact with the interior wall of the pump housing when the rotor spins about its axis during operation. One design for such a rotor is set forth in the aforementioned '314 Publication. Other rotor designs are disclosed in U.S. Published Patent Application No. 2015/0051438, the disclosure of which is also incorporated by reference herein.

A flow straightener 24 is disposed within the pump housing 10 downstream from rotor 20. The flow straightener is fixed to the pump housing 10. The flow straightener 24 has vanes arranged to convert rotation momentum around axis 10 imparted by rotor 20 during operation into momentum in the downstream direction and useful pressure. For example, the flow straightener 24 may have helical vanes having a pitch or direction of twist around axis 16 opposite to the pitch of the blades 20 of the rotor.

Figure 2:
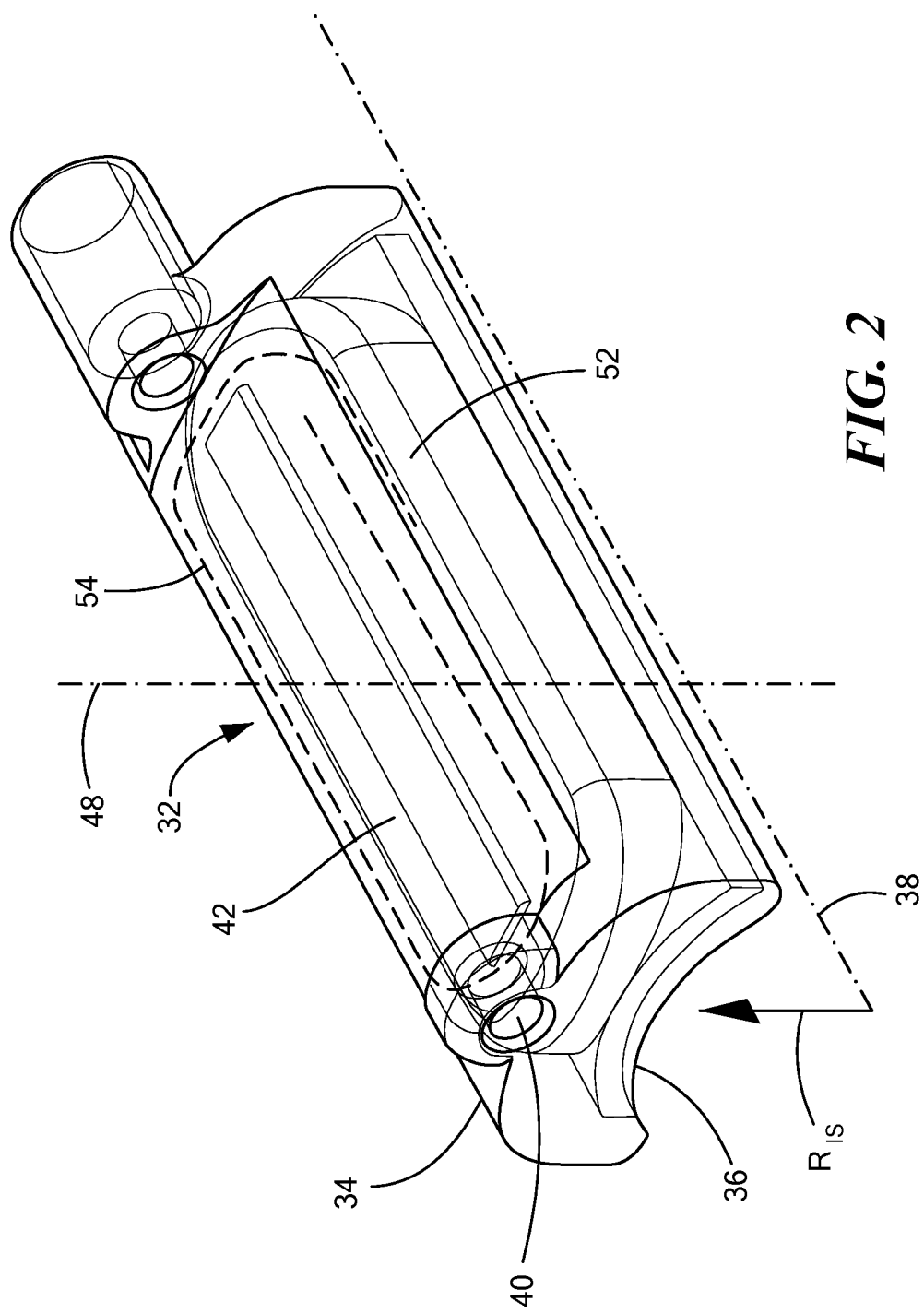
FIG. 2 is a diagrammatic perspective view depicting one element of the pump of FIG. 1, with certain portions depicted as transparent for clarity of illustration.

The pump further includes a stator 30 depicted in a delivery configuration at 30 (to the right in FIG. 1) and in an operative configuration at 30' (to the left in FIG. 1). Stator 30 includes a plurality of coil units 32, in this case, three such units 32a, 32b, and 32c. An individual one of the coil units 32 is depicted in FIG. 2. Each unit 32 of the stator 30 includes a housing 34 having an arcuate inner surface 36 generally in the form of a partial surface of revolution around a unit axis 38. In the embodiments shown, each arcuate inner surface is a sector of a cylinder coaxial with an axis 38. The arcuate inner surface 36 has a radius $R_{is}$ substantially equal to the radius of the outer surface of pump housing 10. Stated another way, the arcuate inner surface 36 is a surface complimentary to a portion of the outer surface of the pump housing 10.

The housing 34 of each unit 32 includes a tubular guide channel 40 extending parallel to the unit axis 38 on the exterior side of the housing, i.e., on the side opposite from arcuate surface 36. A ferromagnetic pole piece 42 is disposed within the housing 34 of each unit 32. The pole piece is a generally rectangular solid having a central axis 48 transverse to the unit axis. The pole piece 42 also includes a wide portion 50 adjacent the inner surface 36. This portion desirably has an interior surface conforming to the interior surface 36 of the housing. The wide portion 50 of the pole piece may define a portion of the interior surface.

A coil 52 includes a plurality of turns 54 of an electrical conductor such as a wire extending around pole piece 42 and axis 48, only one such turn being shown in broken lines in FIG. 2 for clarity of illustration. External conductive leads (not shown) are electrically connected to coil 52. These external leads extend from the housing. The housing protects the coil from the surrounding environment.

Figure 3:
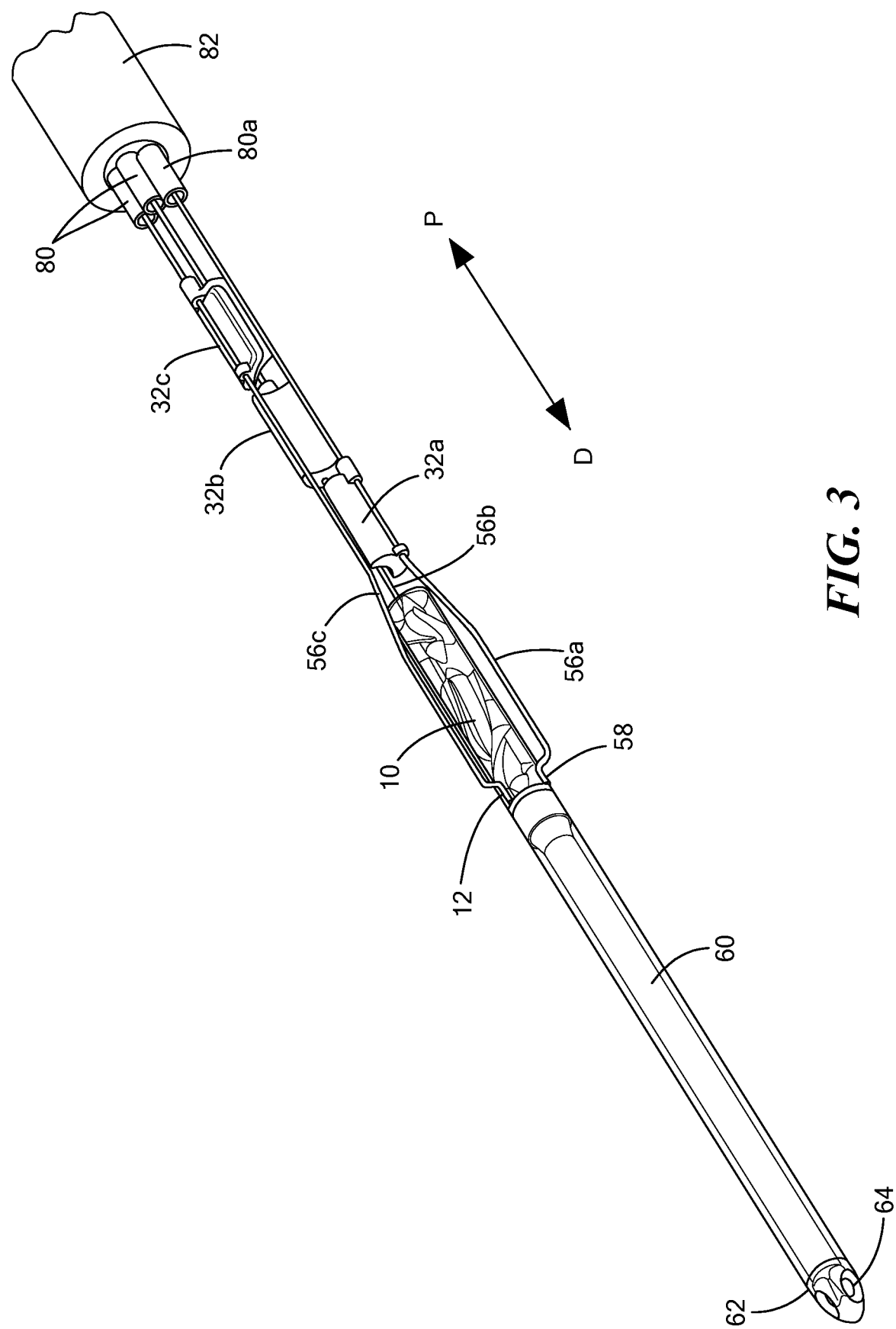
FIG. 3 is a further diagrammatic perspective view depicting elements of the pump and delivery device of FIG. 1 in one condition.

A set of elongated, flexible guides 56a-56c are fastened to the pump housing 10 (FIG. 3). Each guide has a fixed end 58 attached to the pump housing adjacent the inlet end 12 of the housing. The fixed ends 58 of the guides are fastened to the exterior surface of the pump housing at equally spaced intervals around the axis of the pump housing. Each guide extends through the guide channel 40 (FIG. 2) of one stator unit 32. Thus, guide 56a extends through the channel of stator unit 32a (FIG. 3), whereas guide 56b extends through the channel of stator unit 32b, and guide 56c extends through the channel of stator unit 32c.

The external surface of pump housing 10 may have additional guide elements such as small ribs projecting from its outer surface (not shown) and extending generally in the axial direction. These ribs may be arranged to engage the housings of stator units 32a-32b and to guide each such stator unit into the operative position 30' of the stator shown in FIGS. 1-4. Also, the exterior of the pump housing 10 may be provided with one or more stops for arresting motion of each stator unit along the axial direction of the pump housing when the stator unit reaches the operative position as discussed below. A flexible, hollow inlet tube 60 (FIG. 3) is connected to the inlet end 12 of pump housing 10. The tube 60 has a smooth inlet end 62 with opening 64.

The pump can be implanted by a delivery device 70. The delivery device 70 includes a central shaft 72 (FIG. 1) defining a major longitudinal axis extending in a distal direction denoted by arrow D in FIG. 1 and an opposite proximal direction denoted by arrow P. Only the distal end of the shaft is visible in FIG. 1. A fitting 74 at the distal end of shaft 72 defines a conical guide surface 76 flaring outwardly in the distal direction. This guide surface is concentric with central shaft 72. Fitting 74 further defines a seat 78 adapted to engage the outlet end 14 of housing 10 and thus hold the housing on the central shaft with the axis 16 of the housing coaxial with the distal end of shaft 72. The seat 78 desirably is adapted to release from the housing upon command. For example, the housing 10 may have features such as one or more holes or projections (not shown) on its interior or exterior surfaces, and seat 78 may have one or more movable elements such as pins or hooks adapted to engage these features of the housing 10. These elements desirably can be selectively actuated by an operator from the proximal end of the shaft. For example, the shaft 72 may include one or more flexible wires (not shown) extending within it so that movement can be transmitted from the proximal end of the shaft to the hook or pin to release housing 10 from its engagement with seat 78. Any other device capable of actuating an element at a distal end of a shaft can be used. For example, elements driven by fluid pressure, such as balloons, may be used to actuate the release elements of the seat. In other embodiments, housing 10 may be held to seat 78 by one or more sutures that extend through the central shaft 72 or through other elements of the delivery device 70, and the housing may be released from the shaft by pulling on an end of the suture exposed at the proximal end of the shaft. Shaft 72 and fitting 74 are omitted in FIGS. 3 and 4 for clarity of illustration.

In the delivery configuration shown in FIGS. 1 and 3, the units 32a, 32b, and 32c of stator 30 are arranged in a row, i.e. successively, and extend along central shaft 72 and a delivery axis substantially coaxial with the axis of the housing 10. Each unit 32 is offset from the next adjacent unit in the proximal direction indicated by arrow P or in the opposite, distal direction D along the delivery axis. Stated another way, in this embodiment, only one unit 32 is present at any point along the proximal or distal extent of the central shaft 72 and along the delivery axis. Thus, the entire stator 30, in its delivery configuration, has a diameter in a plane transverse to the delivery axis approximately equal to the width of a single stator unit 32 (FIG. 2). As used in this disclose with reference to a structure having a non-circular cross-sectional shape, the term "diameter" refers to the diameter of the smallest circle in a plane perpendicular to the axis of the structure through which the structure can pass.

Figure 4:
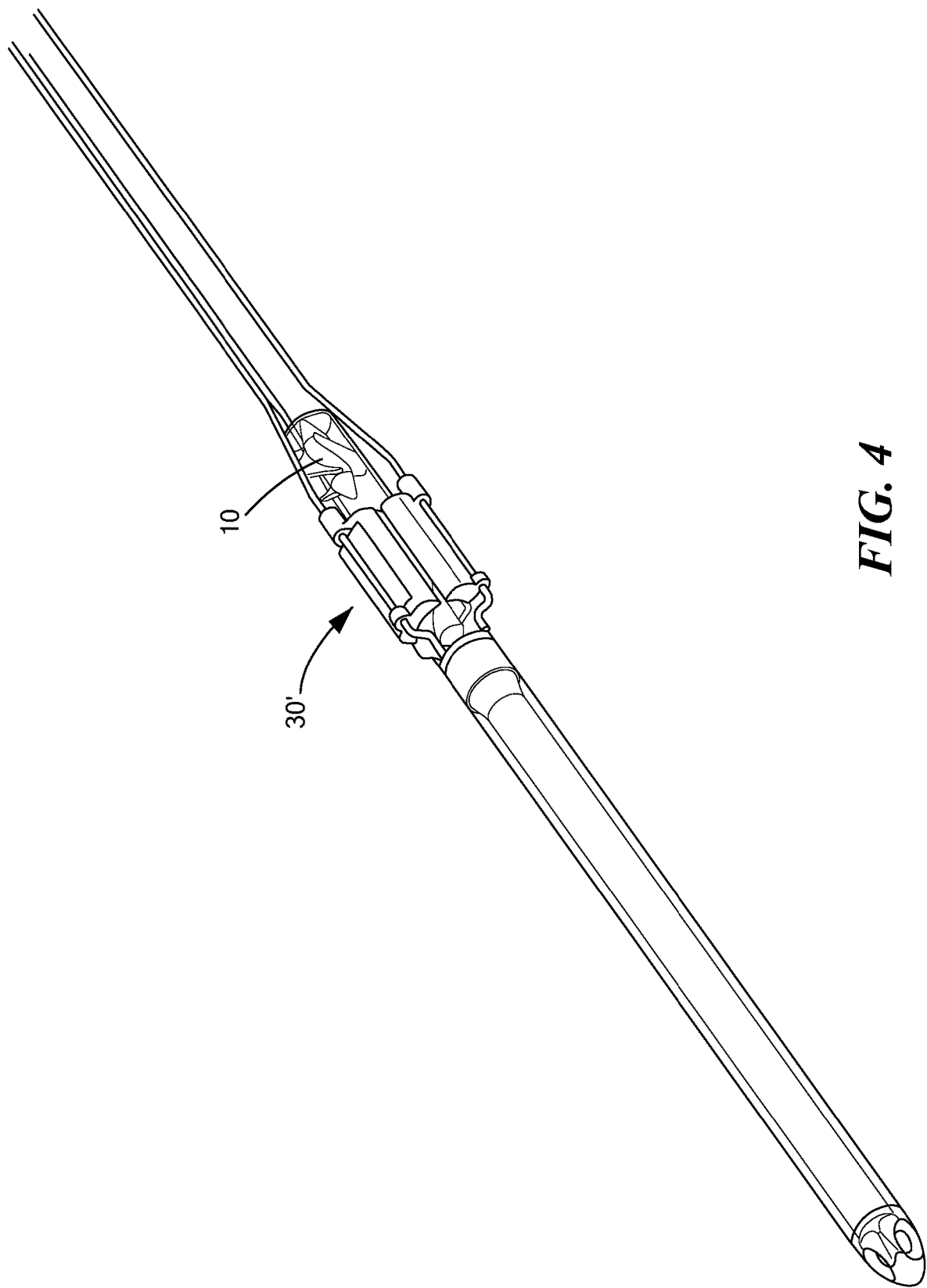
FIG. 4 is a view similar to FIG. 3, but depicting the same elements of the pump in another condition.

The delivery device 70 is also configured to transition the stator units 32 so as to bring the stator 30 from the delivery configuration to the operative configuration illustrated at 30' in FIG. 1 and illustrated in FIG. 4. One structure that is capable of performing this function is schematically indicated in FIG. 3. This structure includes a plurality of hollow pusher shafts 80 disposed within an outer sheath 82. Each such pusher shaft 80 surrounds one of the guides 56a-56c. The central shaft 72 (FIG. 1) is also disposed within outer shaft 82, but is omitted in FIG. 3 for clarity of illustration. A proximal end of each pusher shaft 80 is accessible at the proximal end of the outer shaft 82. Only the distal end of shaft 82 is shown in FIG. 3. While the stator units 32 are in the delivery configuration, the outer shaft 82 may surround the stator units 32 to retain the stator units 32 in position relative to the inner shaft 72. The outer shaft 82 may be retracted proximally relative to the inner shaft 72 and stator units 32 to the position depicted in FIG. 3 to expose the stator units 32. While the outer shaft 82 is so retracted, each pusher shaft 80 can be slid in the distal direction D along the associated guide so as to force one of the stator units 32 from its delivery position to its position in the operative configuration. For example, shaft 80a can be slid along guide 56a to move stator unit 32a distally. As the stator unit 32 moves distally, it slides over the flaring conical surface 76 of fitting 74 and slides over the outer surface of pump housing 10 to its operative position indicated at 32a' in FIG. 1. The other units 32b and 32c can be positioned in their respective final positions by moving the other shafts 80b and 80c in a similar manner. This movement device is merely exemplary. Other mechanisms capable of moving elements at or near the distal end of a delivery device 70 while the distal end is disposed within the body of a subject may be used. For example, resilient elements, shape memory alloys, electrically-actuated mechanisms, and fluid powered elements such as balloons. In a further variant, suture loops may be used to pull, rather than push, the stator units.

When the pump is in its delivery condition, with the stator in the delivery configuration, the pump as a whole has a relatively small diameter. Stated another way, the entire pump can pass through a circle having a diameter equal to or slightly larger than the diameter of pump housing 10 alone. By contrast, when the pump is in an operative condition, with the stator in the operative configuration illustrated at 30' in FIG. 1 and shown in FIG. 4, the diameter of the pump is larger than the diameter of the pump housing.

In a method according to a further aspect of the present disclosure, the pump is implanted into a body of a living subject. While the pump is in its delivery condition, with the pump housing attached to fitting 74 of the central shaft and with the stator in its delivery configuration, the delivery device 70 and pump are advanced into the body of a subject. Typically, the pump is to be implanted in the vascular system and thus is advanced through the vasculature of the subject. For example, the pump may be inserted into a peripheral artery of the subject and advanced towards a target location. Typically, the target location is in the ascending or descending aorta. In one such procedure the pump may be introduced through an opening in the femoral artery through a small incision in the skin. In other cases, the pump may be introduced into an artery through an aortotomy in an artery remote from the aorta and again advanced through the arteries toward the aorta until the pump reaches a target location. When the pump is position in the ascending aorta, the inlet tube 60 (FIGS. 3-4) may extend through the aortic valve into the left ventricle of the heart. Even where the particular dimensions of the subject or the target location for the pump preclude advancement through the vasculature, the small delivery diameter facilitates advancement of the pump into the subject's body. For example, the pump may be placed through a surgically created opening in the patient's heart and advanced through the heart or through another organ to the target location.

Once the pump is at or near the target location, the delivery device 70 is actuated to bring the stator to its operative configuration and thus bring the pump to the operative condition. For example, outer sheath 82 may be retracted to expose the stator units, and pusher tubes 80 may be advanced distally to move the stator units 32 to the operative position 30' shown in FIG. 4. Fitting 74 (FIG. 1) on the inner shaft 72 is disengaged from the housing 10 of the pump, and the delivery device 70 is removed. The leads (not shown) associated with the stator units may be left in place, extending through the vasculature to the location where the delivery device 70 was inserted into the vasculature, and may be connected to a conventional controller (not shown) adapted to provide power to the stator units. The guides 56a-56c may remain in place or may be removed. With the stator units the operative position, in place around the pump housing, electrical power is applied to the coils in the normal manner, through the leads associated with the stator units. The electrical current within the coils of the stator units creates a rotating magnetic field turning around axis 16 of the pump housing. This rotating field drives the rotor and causes the rotor to impel blood through the pump, from inlet cannula 62 to the outlet of the pump housing.

The pump optionally may include a device such as an expandable anchor (not shown) attached to the pump housing 10 or to one or more of the stator units. As described, for example, in the aforementioned '312 Publication, such an expandable anchor may hold the pump in location as, for example, at a target location in the aorta. Desirably, the expandable anchor is in a collapsed condition when the pump is advanced into the vasculature.

Numerous variations and combinations of the features discussed above can be used. For example, a pump according to a further embodiment of the invention has a stator with a delivery configuration shown in FIG. 5 and an operative configuration shown in FIG. 6. The stator 130 includes plural stator units 152 similar to the stator units discussed above. In the delivery configuration 130 (FIG. 5), the stator units are not arranged in a row, but rather are stacked on one another. The stator units are connected to one another by one or more elements 101 formed from deformable material. Each such element may be a web or mesh of a shape memory alloy as, for example, a nitinol alloy. Each such element 101 is arranged to deform spontaneously from its shape as shown in the delivery configuration to an operative shape 101' (FIG. 6). For example, the shape memory alloy may be arranged to deform upon exposure to body temperature. Alternatively, the shape memory alloy may be arranged to deform to the operative position under its own elasticity and may be restrained in the delivery configuration by the delivery device 70. The stator in its operative condition 130' forms a generally tubular unit with an interior space between the stator units. In the operative configuration, the stator may be slid onto the outside of the pump housing, so that the pump housing is received within this generally tubular unit.

Figure 7:
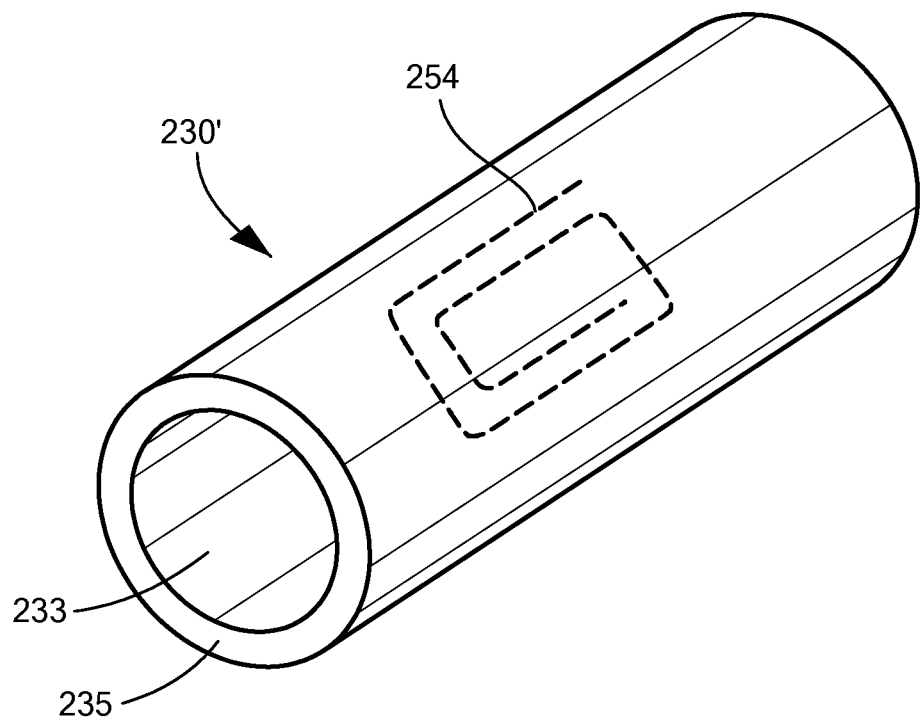
FIG. 7 is a diagrammatic perspective view depicting an element of a pump according to yet another embodiment of the invention in one condition.
Figure 8:
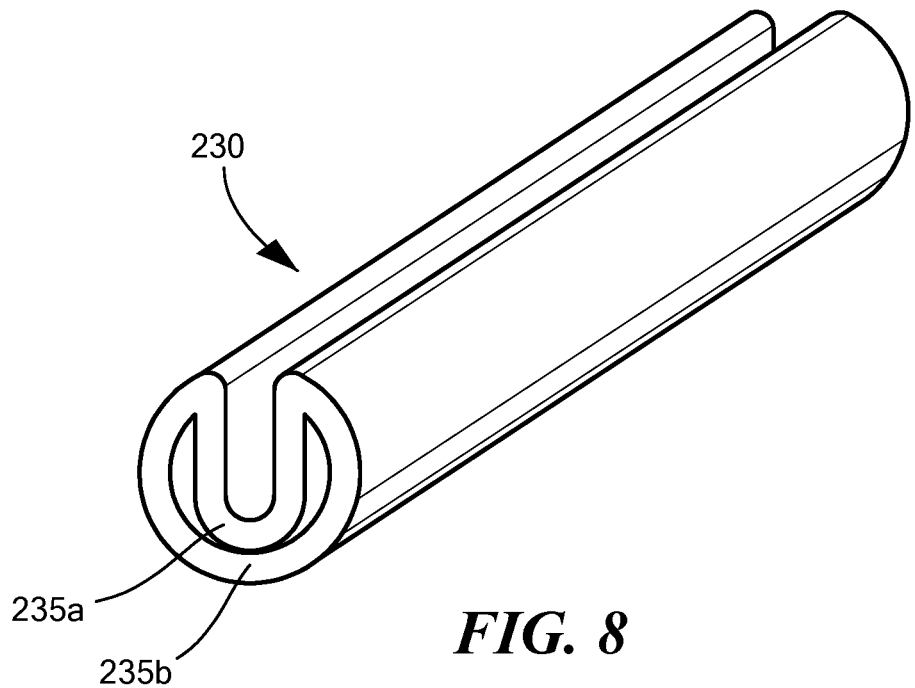
FIG. 8 is a view similar to FIG. 7 and depicting the same element in another condition.

In a further variant (FIGS. 7-8), a stator in its operative condition includes a generally tubular housing having a wall 235 defining an interior bore 233. Coils 254, one of which is schematically depicted in FIG. 7, are embedded within the wall 235. In the delivery configuration, the stator is compressed by folding wall 235 generally along lines parallel to the axis of the tubular housing so as to bring one portion 235a of the wall close to another portion 235b, within the space normally occupied by bore 233, and thus compress the stator to a smaller diameter. The stator according to this embodiment may omit the ferromagnetic cores usually present in the stator coils. The stator 230 may be brought to the operative configuration 230' by the resilience of the wall. For example, the stator may be constrained by a sheath incorporated in the delivery device 70 and may revert to the operative configuration when the stator is ejected from the sheath. Alternatively, a mechanical expansion device or an inflatable device such as a balloon may be disposed within the stator. The balloon is inflated to bring the stator to its operative condition.

Where ferromagnetic cores are provided in the stator (as in the embodiment discussed above with reference to FIGS. 1-4), magnetic attraction between the poles of the magnet incorporated in the rotor and the ferromagnetic cores can maintain the axial position of the rotor with respect to the housing. If the ferromagnetic cores are omitted, the housing may incorporate ferromagnetic elements to perform a similar function. Alternatively or additionally, the rotor may be provided with hydrodynamic thrust bearings and the housing may be provided with complementary surfaces so that hydrodynamic action maintains the rotor in position relative to the housing. In still other embodiments, the housing and rotor may incorporate mechanical bearings to or to control the axial position of the rotor relative to the housing, to maintain the rotor coaxial with the stator, or both.

As these and other variations and combinations of the features described hereinabove may be used, the foregoing description should be taken by way of illustration rather than by way of limitation of the present disclosure.

What is claimed is:

1. A blood pump, comprising:
   a housing having an interior and an exterior, the housing defining a housing axis and an axial direction along the housing axis;
   a pump rotor configured to be received within the interior of the housing, the pump rotor including a magnet; and
   a stator having a plurality of stator units, each stator unit having a coil and a delivery configuration and an operative configuration, the plurality of stator units in the delivery configuration having a delivery diameter, each stator unit being configured to slide successively along a common shaft, the plurality of stators units in the operative configuration being configured to:
be disposed around the exterior of the housing; and
form an assembled pump having a diameter greater than the delivery diameter.

2. The blood pump of claim 1, wherein the housing defines a housing axis and axial directions along the housing axis, each coil within each unit of the plurality of stator units including a coil axis and an electrical conductor arranged in one or more turns surrounding the coil axis, the stator in the operative configuration having the units disposed around the housing axis with the coil axes of the units transverse to the housing axis.

3. The blood pump of claim 2, wherein in the delivery configuration:
the stator has a delivery axis;
the coil axes are transverse to the delivery axis; and
at least one of the units is offset from another one of the units in a direction along the delivery axis.

4. The blood pump of claim 3, wherein in the delivery configuration the units of the stator are disposed in a row along the delivery axis, with each of the units being offset from an adjacent one of the units in a direction along the delivery axis.

5. The blood pump of claim 3, wherein the housing has an exterior surface including one or more arcuate surfaces coaxial with the housing axis, and wherein each of the units has an interior surface in the form of a partial surface of revolution around a unit axis transverse to the coil axis of that unit, the interior surfaces of each units confronting the arcuate surfaces of the housing when the stator is in the operative configuration.

6. The blood pump of claim 1, wherein the stator includes a flexible member including one or more coils, the flexible member extending around the housing when the stator is in the operative condition.

7. The blood pump of claim 6, wherein when the stator is in the operative configuration, the flexible member forms a tube and the pump housing is disposed within the tube, and wherein the flexible member is folded when the stator is in the delivery configuration.

8. A blood pump implantation assembly, comprising:
a delivery device;
a pump mounted to the delivery device proximate a distal end thereof, the pump including a pump housing, a rotor configured to be disposed within the pump housing and a stator having stator units, the pump in the operative configuration having the units disposed around the housing axis with the coil axes of the units transverse to the housing axis;
the pump in a delivery condition having the stator units offset from the pump housing and having the stator define a first diameter, the delivery device being configured to transition the pump from the delivery condition to an operative condition in which the stator is in an operative configuration disposed around the pump housing and defines a second diameter larger than the first diameter, each stator unit being configured to slide successively along a common shaft in the delivery condition.

9. The assembly of claim 8, wherein the housing has a housing axis extending proximally and distally when the pump is in the delivery condition, the stator including a plurality of units, each unit including a coil having a coil axis and an electrical conductor arranged in one or more turns surrounding the coil axis.

10. The assembly of claim 9, wherein in the delivery configuration the coil axes are transverse to a major longitudinal axis of the delivery device and at least one of the units is offset from another one of the units along the major longitudinal axis.

11. The assembly of claim 10, wherein in the delivery configuration the units of the stator are arranged successively along the major longitudinal axis.

12. The assembly of claim 11, wherein the delivery device is configured to advance the units along the major longitudinal axis toward the pump housing to bring the pump from the delivery condition to the operative condition.

13. The assembly of claim 8, wherein the stator includes a flexible member including one or more coils, the flexible member extending around the housing when the pump is in the operative condition.

14. The assembly of claim 13, wherein the flexible member is a tube having a wall, the wall defining a bore and the housing being disposed within the bore when the pump is in the operative condition, the flexible member being folded along one or more fold axes when the pump is in the delivery configuration.

15. The assembly of claim 8, wherein the pump is releasably mounted to the delivery device.

16. A method of implanting a blood pump in the body of a living subject, comprising:
advancing the pump into the body of the subject to a target location, the pump being in a delivery condition in which a stator of the pump having stator units is separate from a pump housing and the pump has a delivery diameter; and
sliding the stator units successively along a common shaft; and
transitioning the pump to an operative condition, the stator being disposed around the pump housing and the pump has an operative diameter greater than the delivery diameter when in the operative condition.

17. The method of claim 16, further comprising applying electrical power to the stator to provide a rotating magnetic field within the housing while the pump is in the operative condition a rotor within the housing is rotated and the rotor impels blood through the housing.

18. The method of claim 17, wherein advancing the pump into the body of the subject to a target location step includes advancing the pump through vasculature of the subject.

19. The method of claim 16, wherein transitioning the pump to an operative condition includes at least one from the group consisting of retracting and advancing a portion of a delivery device, the delivery device including the stator in the delivery condition.

* * * * *